United States Patent
Gonzalez et al.

(12)

(10) Patent No.: US 6,328,689 B1
(45) Date of Patent: Dec. 11, 2001

(54) LUNG CONSTRICTION APPARATUS AND METHOD

(75) Inventors: Hugo X. Gonzalez, Woodinville; Diane M. Muff, Bellevue; William A. Sirokman, Kirkland, all of WA (US)

(73) Assignee: Spiration, Inc.,, Redmond, WA (US)

( * ) Notice: Subject to any disclaimer, the term of this patent is extended or adjusted under 35 U.S.C. 154(b) by 0 days.

(21) Appl. No.: 09/534,244

(22) Filed: Mar. 23, 2000

(51) Int. Cl.$^7$ .............................. A61F 2/00; A61H 19/00
(52) U.S. Cl. ............................... 600/37; 601/153
(58) Field of Search ............... 600/16, 37; 607/2; 128/898; 452/116; 601/153

(56) References Cited

U.S. PATENT DOCUMENTS

| | | | |
|---|---|---|---|
| 5,167,568 | * 12/1992 | Esbroeck et al. | 452/116 |
| 5,507,797 | 4/1996 | Suzuki et al. | 606/140 |
| 5,558,617 | * 9/1996 | Heilman et al. | 600/16 |
| 5,702,343 | * 12/1997 | Alferness | 600/37 |
| 6,076,013 | * 6/2000 | Brennan et al. | 607/2 |
| 6,085,754 | * 7/2000 | Alferness et al. | 128/898 |
| 6,095,968 | * 8/2000 | Snyders | 600/16 |
| 6,123,663 | 9/2000 | Rebuffat . | |
| 6,155,968 | * 12/2000 | Wilk | 600/16 |

* cited by examiner

*Primary Examiner*—Eric F. Winakur
*Assistant Examiner*—Nikita R Veniaminov
(74) *Attorney, Agent, or Firm*—Graybeal Jackson Haley LLP

(57) ABSTRACT

A lung constriction device and method provide lung air leak suppression or lung volume reduction. The lung constriction device includes a jacket of flexible material. The jacket is configured to cover at least a portion of a lung. The jacket is further configured to receive the lung portion as it is drawn therein. The jacket may be expandable and held in an expanded condition as the lung tissue is drawn into the jacket. Thereafter, the jacket is permitted to collapse about the lung portion to constrict the lung portion. The jacket may alternatively be nonexpandable. As the lung tissue is drawn into the jacket, it will collapse. Once disposed in the jacket, the jacket constricts the lung tissue to provide leakage suppression or lung volume reduction. The jacket may further be severable so that after the lung portion is drawn into the jacket, the jacket may be severed to section the lung portion.

41 Claims, 9 Drawing Sheets

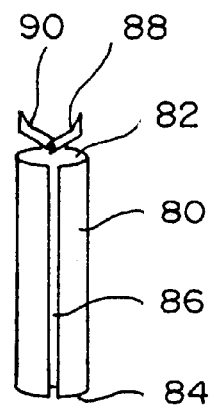
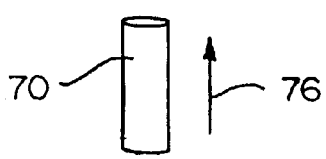
FIG. 6
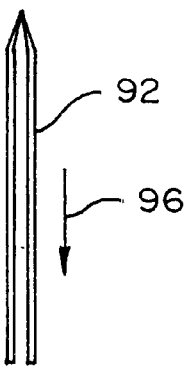
FIG. 7
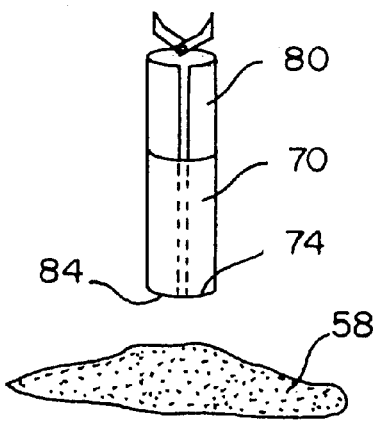

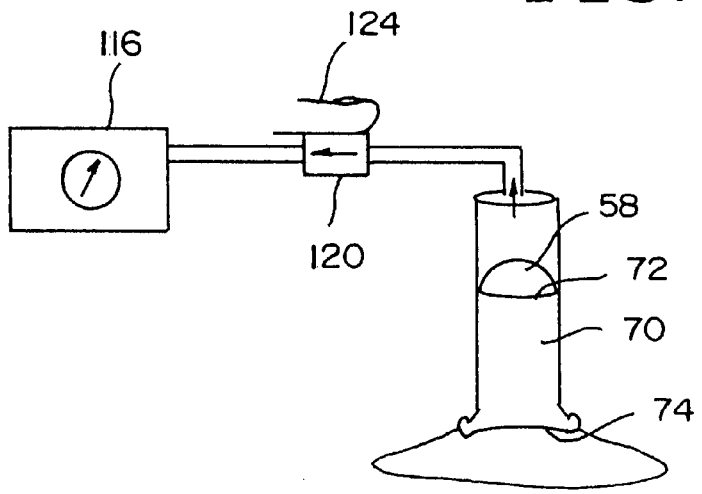
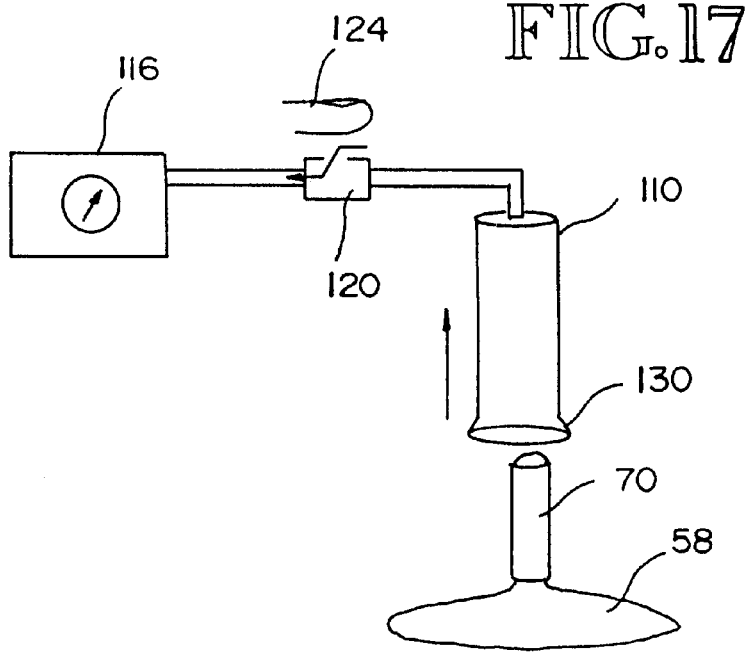

LUNG CONSTRICTION APPARATUS AND METHOD

BACKGROUND OF THE INVENTION

The present invention is generally directed to an apparatus and method for constricting at least a portion of a lung and which may be used for suppressing air leakages in lung tissue or for treating Chronic Obstructive Pulmonary Disease (COPD). The present invention is more particularly directed to such an apparatus which may be implanted in the human body and to a method for readily applying the apparatus to at least a portion of a lung.

Chronic Obstructive Pulmonary Disease (COPD) has become a major cause of morbidity and mortality in the United States over the last three decades. COPD is characterized by the presence of airflow obstruction due to chronic bronchitis or emphysema. The airflow obstruction in COPD is due largely to structural abnormalities in the smaller airways. Important causes are inflammation, fibrosis, goblet cell metaplasia, and smooth muscle hypertrophy in terminal bronchioles.

The incidence, prevalence, and health-related costs of COPD are on the rise. Mortality due to COPD is also on the rise. In 1991 COPD was the fourth leading cause of death in the United States and had increased 33% since 1979.

COPD affects the patient's whole life. It has three main symptoms: cough; breathlessness; and wheeze. At first, breathlessness may be noticed when running for a bus, digging in the garden, or walking up hill. Later, it may be noticed when simply walking in the kitchen. Over time, it may occur with less and less effort until it is present all of the time.

COPD is a progressive disease and currently has no cure. Current treatments for COPD include the prevention of further respiratory damage, pharmacotherapy, and surgery. Each is discussed below.

The prevention of further respiratory damage entails the adoption of a healthy lifestyle. Smoking cessation is believed to be the single most important therapeutic intervention. However, regular exercise and weight control are also important. Patients whose symptoms restrict their daily activities or who otherwise have an impaired quality of life may require a pulmonary rehabilitation program including ventilatory muscle training and breathing retraining. Long-term oxygen therapy may also become necessary.

Pharmacotherapy may include bronchodilator therapy to open up the airways as much as possible or inhaled β-agonists. For those patients who respond poorly to the foregoing or who have persistent symptoms, Ipratropium bromide may be indicated. Further, courses of steroids, such as corticosterocds, may be required. Lastly, antibiotics may be required to prevent infections and influenza and pneumococcal vaccines may be routinely administered. Unfortunately, there is no evidence that early, regular use of pharmacotherapy will alter the progression of COPD.

Lung transplantation is also an option. Today, COPD is the most common diagnosis for which lung transplantation is considered. Unfortunately, this consideration is given for only those with advanced COPD. Given the limited availability of donor organs, lung transplant is far from being available to all patients.

About 40 years ago, it was first postulated that the tethering force that tends to keep the intrathoracic airways open was lost in emphysema and that by surgically removing the most affected parts of the lungs, the force could be partially restored. Although the surgery was deemed promising, the procedure was abandoned.

The lung volume reduction surgery (LVRS) was later revived. In the early 1990's, hundreds of patients underwent the procedure. However, the procedure has fallen out of favor due to the fact that Medicare stopped remitting for LVRS. Unfortunately, data is relatively scarce and many factors conspire to make what data exists difficult to interpret. The procedure is currently under review in a controlled clinical trial. However, what data does exist tends to indicate that patients benefited from the procedure in terms of an increase in forced expiratory volume, a decrease in total lung capacity, and a significant improvement in lung function, dyspnea, and quality of life.

Improvements in pulmonary function after LVRS have been attributed to at least four possible mechanisms. These include enhanced elastic recoil, correction of ventilation/perfusion mismatch, improved efficiency of respiratory musculature, and improved right ventricular filling.

The improvements in pulmonary function resulting from LVRS cannot be ignored. However, the surgery is very invasive and fraught with complications.

Among the complications is the potential for lung air leaks. Lung tissue is very thin, and fragile hence difficult to suture together. After a lung portion is sectioned and removed, the remaining lung is most often restructured with suture staples. In about thirty percent (30%) of the cases, the difficulty with suturing lung tissue results in air leaks. Treatment for such air leaks depends upon their severity and often, in the most serious cases, requires further open chest surgery.

Air leaks in lungs can be caused by other causes. With increasing age, a patient may develop a weakened section of lung which may then rupture due to an extreme pressure differential, such as may result from simply a hard sneeze. AIDS patients can suffer from air leaks in their lungs. Air leaks in lungs can further be caused by a puncture from a broken rib or a stab wound.

The present invention provides a lung constriction device and method for suppressing such air leaks in lung tissue. The air leak suppression, in accordance with the present invention, does not require any suturing of the effected lung tissue. Still further, by constricting a large enough portion of a lung in accordance with the present invention, lung volume reduction with the concomitant improved pulmonary function may be obtained without the need for any suturing of lung tissue at all.

SUMMARY OF THE INVENTION

The invention provides a lung constriction device including a jacket of flexible material configured to cover at least a portion of a lung. The jacket has a pair of opened ends to permit the lung portion to be drawn into the jacket. The jacket is dimensioned to constrict the lung portion after the lung portion is drawn therein.

The invention still further provides a lung constriction device including a member formed of expandable material, the member being configured for receiving a lung portion when forced into an expanded enlarged condition by an expansion force, and contractible about the lung portion upon release of the expansion force for constricting the lung portion.

The invention still further provides a method of constricting at least a portion of a lung. The method includes the steps of providing a jacket formed of flexible material and configured to cover the lung portion and drawing the lung portion into the jacket. The jacket may be formed of expandable flexible material to expand the jacket into an expanded condition, while drawing the lung portion into the jacket. The expansion of the jacket may thereafter be released to permit the jacket to contract about the lung portion and constrict the lung.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

FIG. 6 illustrates a lung constriction device embodying the present invention and a mandrel which may be used in a mechanical method embodying the present invention for deploying the constriction device;

FIG. 7 illustrates an initial step in practicing the mechanical method of deployment embodying the present invention;

FIG. 16 illustrates an intermediate step in the still further method embodiment of deploying the lung constriction device;

FIG. 17 illustrates a final step in the still further method embodiment of deploying the lung constriction device;

DETAILED DESCRIPTION

Figure 1:
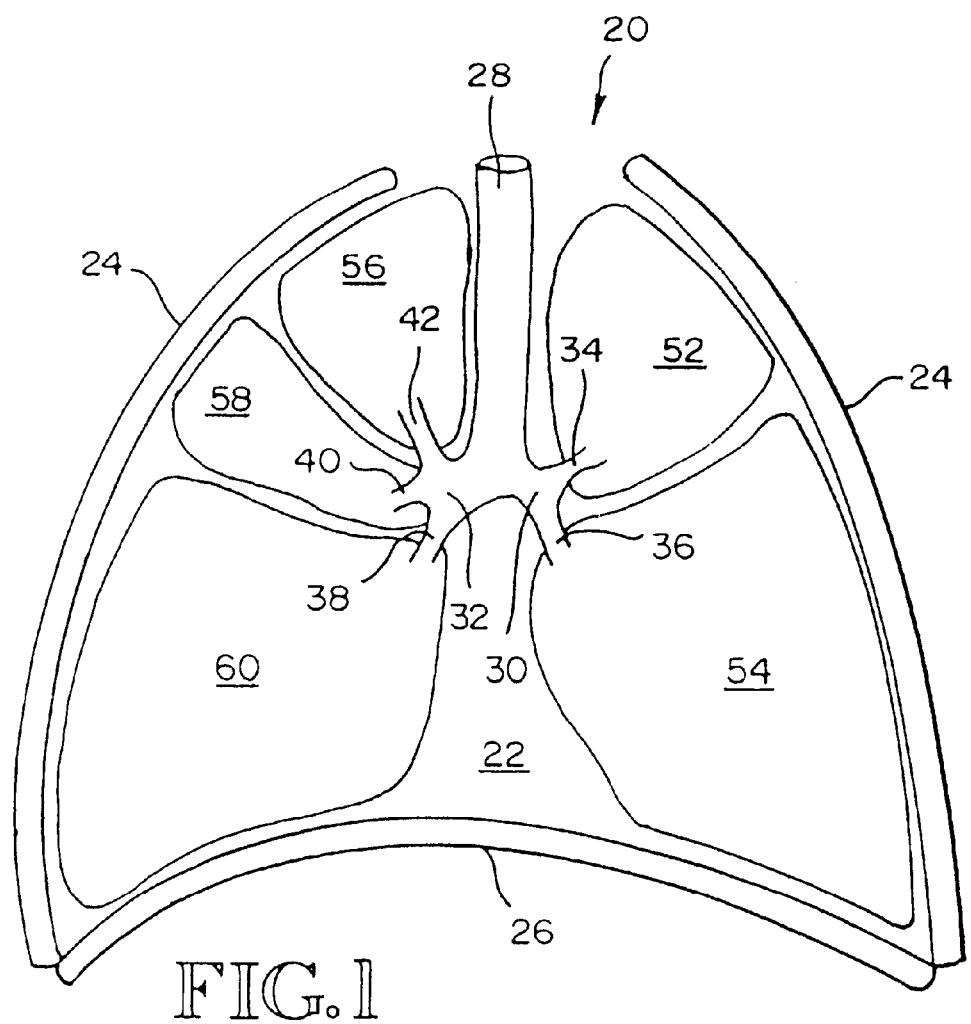
FIG. 1 is a simplified sectional view of a thorax illustrating a healthy respiratory system.

Referring now to FIG. 1, it is a sectional view of a healthy respiratory system. The respiratory system 20 resides within the thorax 22 which occupies a space defined by the chest wall 24 and the diaphragm 26.

The respiratory system 20 includes the trachea 28, the left mainstream bronchus 30, the right mainstream bronchus 32, and the bronchial branches 34, 36, 38, 40, and 42. The respiratory system 20 further includes left lung lobes 52 and 54 and right lung lobes 56, 58, and 60. Each bronchial branch communicates with a respective different portion of a lung lobe, either the entire lung lobe or a portion thereof.

A healthy respiratory system has an arched or inwardly arcuate diaphragm 26. As the individual inhales, the diaphragm 26 straightens as illustrated in FIG. 1 to increase the volume of the thorax 22. This causes a negative pressure within the thorax. The negative pressure within the thorax in turn causes the lung lobes to fill with air to an inflated condition as illustrated in FIG. 1. When the individual exhales, the diaphragm returns to its original arched condition to decrease the volume of the thorax. The decreased volume of the thorax causes a positive pressure within the thorax which in turn causes exhalation of the lung lobes.

Figure 2:
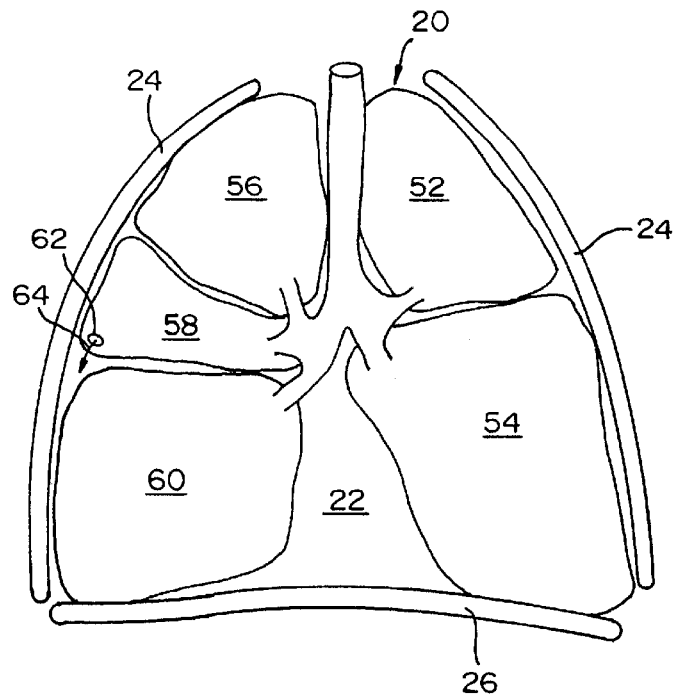
FIG. 2 is a sectional view similar to FIG. 1 but illustrating a respiratory system suffering from an air leak in a lung lobe.
Figure 3:
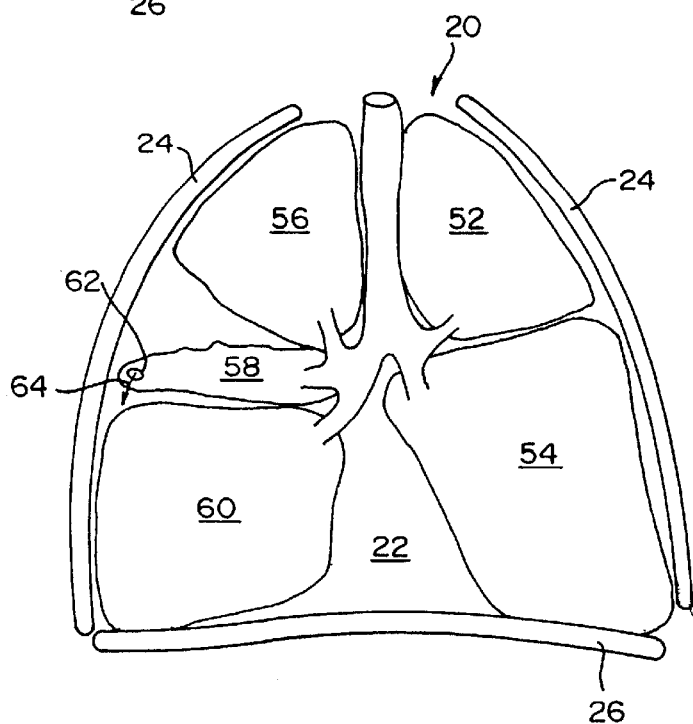
FIG. 3 is a sectional view illustrating the lung lobe having the air leak in a deflated condition due to the air leak.

FIG. 2 illustrates the respiratory system 20 just after suffering an air leak or rupture. Here it may be seen that the rupture 62 has occurred in lung lobe 58. As a result, air is escaping from the lung lobe 58 as indicated by the arrow 64. Hence, this individual is incapable of breathing normally. The negative pressure created by the moving diaphragm 26 causes some of the air taken into lobe 58 to be lost through the rupture 62. When the diaphragm 26 returns to its arched configuration, the positive pressure produced thereby forces still more air from lobe 58 through the rupture. Eventually, within a short time, the lobe 58 collapses as illustrated in FIG. 3 and becomes nonfunctional to support respiration.

Figure 4:
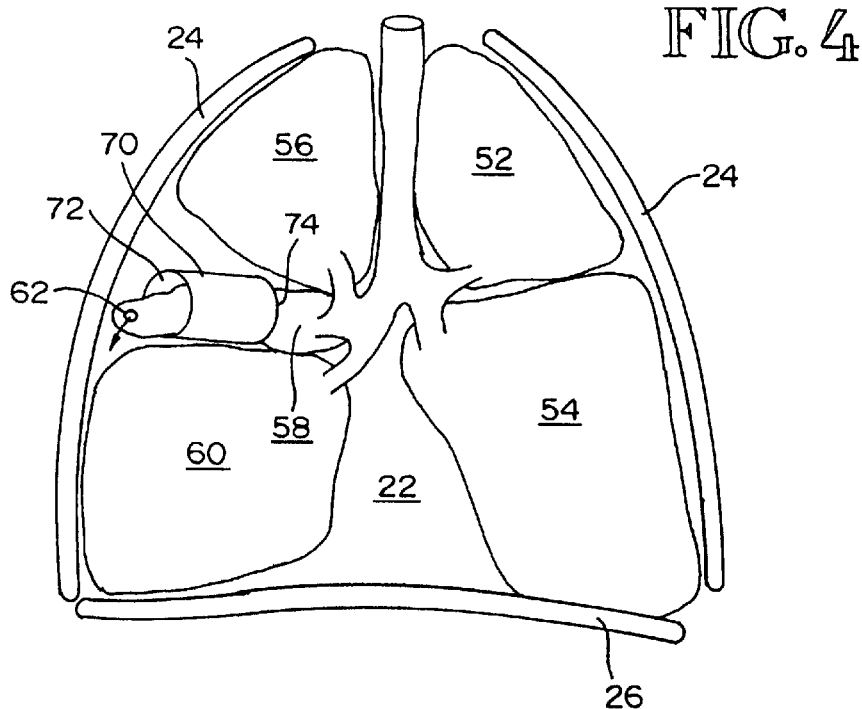
FIG. 4 is a sectional view of the respiratory system of FIG. 2 with a lung constriction apparatus embodying the present invention being disposed over a lung portion to be constricted for suppressing the air leak.

FIG. 4 shows a lung constriction device 70 embodying the present invention in the process of being deployed on the effected lung lobe 58. The device 70 is configured as a jacket formed of a sheet or flexible fabric of biocompatible material. The material may be both flexible and expandable material formed from silicone rubber, polyurethane, expanded polytetraflouroethylene, polyester and polyurethane, or nylon and polyurethane, for example. It may alternatively be flexible but nonexpandable formed from nylon, polytetraflouroethylene, or polyester, for example. If the jacket is expandable, it may more specifically be formed from a sheet or fabric of 70% nylon and 30% polyurethane. The jacket is preferably opened at both ends 72 and 74 and, as illustrated, may be generally cylindrical in configuration.

Figure 5:
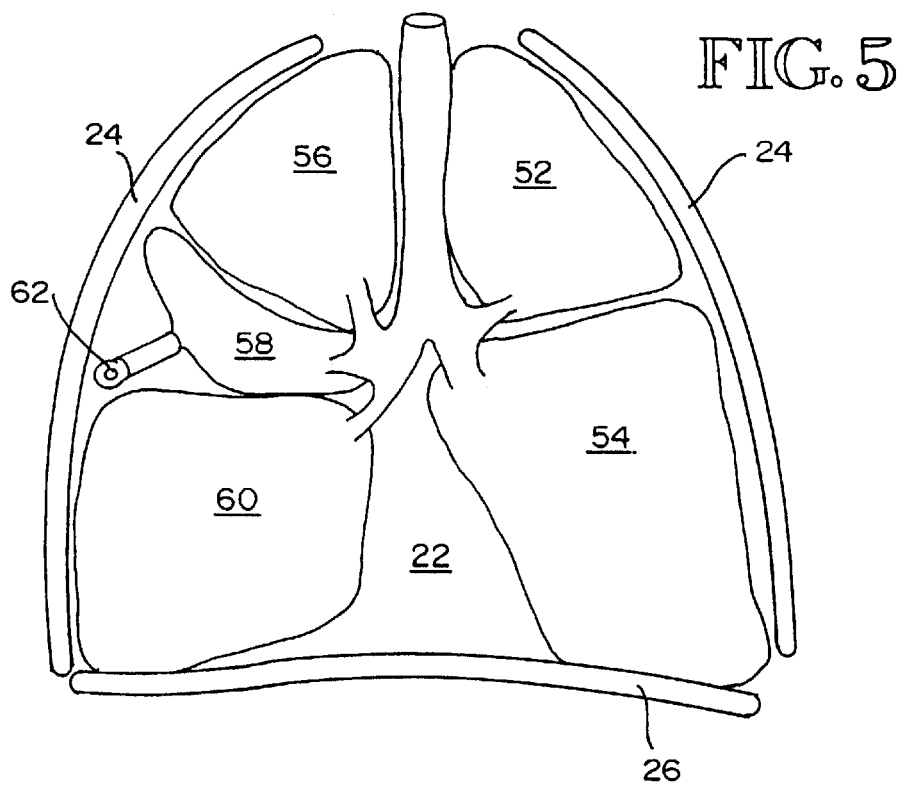
FIG. 5 is a sectional view illustrating the lung constricting apparatus constricting the effected lung portion and suppressing the air leak.

In accordance with one embodiment of the present invention, the jacket is applied to the portion of the lung lobe having the leak or puncture while the jacket is in an expanded condition. This may be accomplished, as will be seen hereinafter, by expanding the jacket and then pulling the lung portion into the jacket. When the effected lung portion is thus disposed with respect to the jacket as illustrated in FIG. 4, the expansion of the device is released as seen, for example, in FIG. 5. With the expansion released, the jacket is permitted to contract or collapse about the lung portion to constrict the lung portion and effectively suppress the leak or puncture.

In accordance with a further embodiment, if the flexible jacket is nonexpandable, the lung tissue may be collapsed as it is pulled into the jacket. Once disposed in the jacket, the lung tissue will remain constricted by the jacket.

When the lung portion is thus constricted, the air leakage will be suppressed. The lung lobe 58 thereafter, during successive breaths, will reinflate and become functional once again to support respiration.

The use of the device 70 need not be restricted to the suppression of air leakages in lungs. It may, for example, find use to advantage in constricting a lung portion suffering from COPD to simulate or achieve lung volume reduction. All of the beneficial effects of lung volume reduction surgery may be realized and, most importantly, without requiring suturing of lung tissue.

FIGS. 6–11 illustrate a mechanical process for deploying the lung constriction device 70. In an initial step, as illustrated in FIG. 6, the device 70 is first aligned with an expansion mandrel or form 80. The device 70 is then moved towards the form 80 as indicated by the arrow 76.

In accordance with this embodiment, the form 80 is hollow, has opened ends 82 and 84 and has a configuration similar to that of the device 70. In addition, the form has a longitudinal slit 86 rendering the form expandable in a transverse direction. The form further includes tabs 88 and 90 which, when pressed towards each other, cause the form to expand in the transverse direction.

Figure 8:
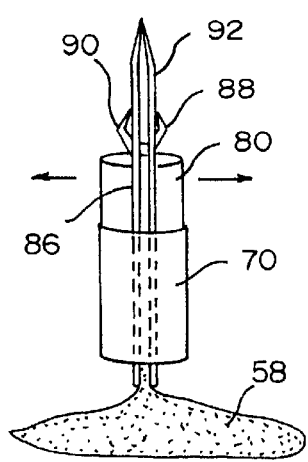
FIG. 8 illustrates a further step in the mechanical deployment of the constriction device.

The device 70 is applied to the form 80 until the end 74 of the device 70 is at the end 84 of the form 80 as illustrated in FIG. 7. An atraumatic instrument, such as a forceps 92, is then aligned with the form 80 and moved relative thereto through the form in the direction of arrow 96 and into engagement with the lung tissue 58 as illustrated in FIG. 8.

Figure 9:
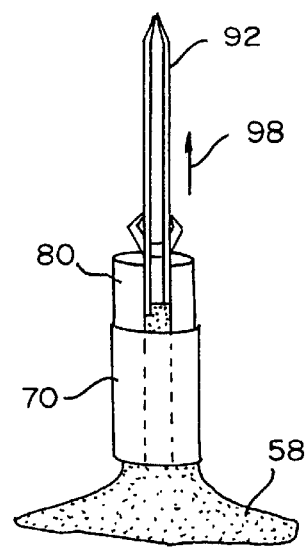
FIG. 9 illustrates the step of pulling the lung portion to be constricted into the constriction device in accordance with the mechanical method embodiment.

The forceps 92 are then used to grab the lung tissue 58. Then, the tabs 88 and 90 of the form 80 are pressed toward each other to cause the form 80 to expand in a transverse direction. This may be noticed by the longitudinal slit 86 becoming noticeably wider. The expansion of the form 80 in the transverse direction imparts an expansion force on the device 70, causing it to similarly expand to an expanded condition. With the device 70 thus expanded, the forceps are then retracted as illustrated in FIG. 9 in the direction of arrow 98, to pull the lung tissue into the form 80 and device 70. Preferably, although not necessarily, the lung tissue is pulled until it extends entirely through the device 70.

Figure 10:
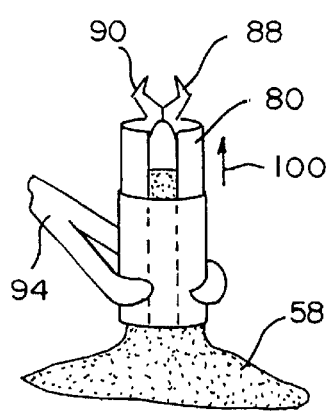
FIG. 10 illustrates the manner in which an expansion force may be released from the constriction device as a final step in deploying the constriction device in accordance with the mechanical method embodiment.

The process continues as illustrated in FIG. 10. Here, the tabs 88 and 90 are released. Given the volume of lung tissue within the form 80 and device 70, the device 70 remains in an expanded condition. Now, a suitable instrument 94 is used to hold the device 70 in place while the form 80 is moved in the direction of the arrow 100 to withdraw the form 80 from the device 70.

Figure 11:
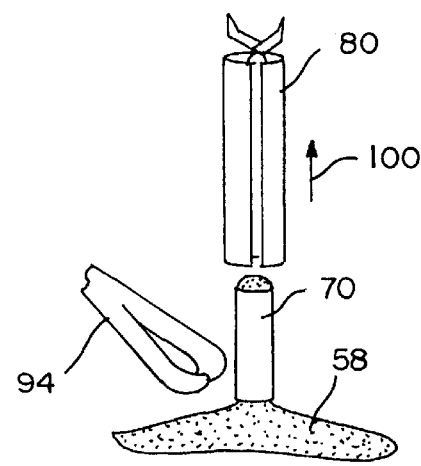
FIG. 11 illustrates the constriction device fully deployed as a result of the mechanical method embodiment illustrated in FIGS. 6–10.

As illustrated in FIG. 11, the process is completed when the form 80 is totally withdrawn from the device 70. In doing so, the expansion force applied to the device 70 by the form 80 is released, permitting the device 70 to collapse or contract about the lung tissue 58 drawn into the device 70. The device 70 now constricts the lung tissue to effect air leak suppression or lung volume reduction, for example.

Alternatively, the form 80 need not be expandable if the device 70 is not expandable. Here, the process of pulling the lung tissue into the mandrel 80 and device 70 will cause the lung tissue to collapse. With the device 70 being dimensioned for constricting the lung tissue, once the mandrel is removed, the lung tissue will remain in and be constricted by the device 70 as illustrated in FIG. 11.

Figure 12:
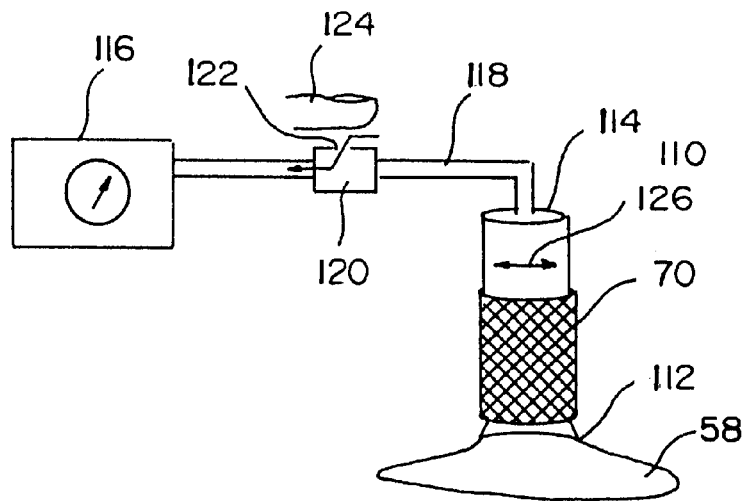
FIG. 12 illustrates an initial step of a further method of deploying the lung constriction device in accordance with further aspects of the present invention.
Figure 13:
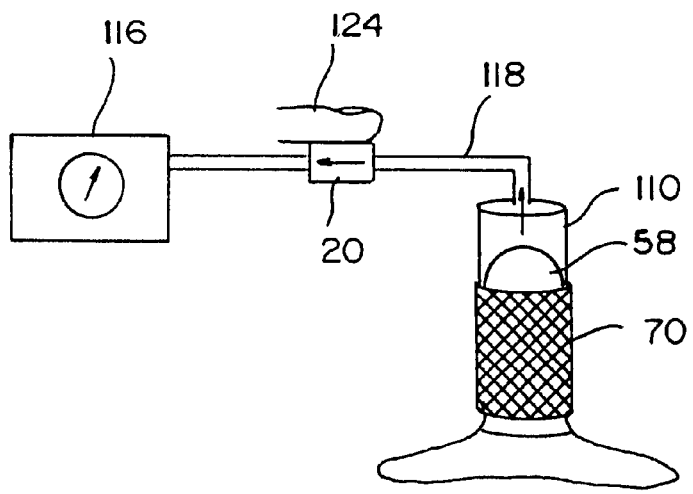
FIG. 13 illustrates an intermediate step in the further method embodiment of deploying the lung constriction device.
Figure 14:
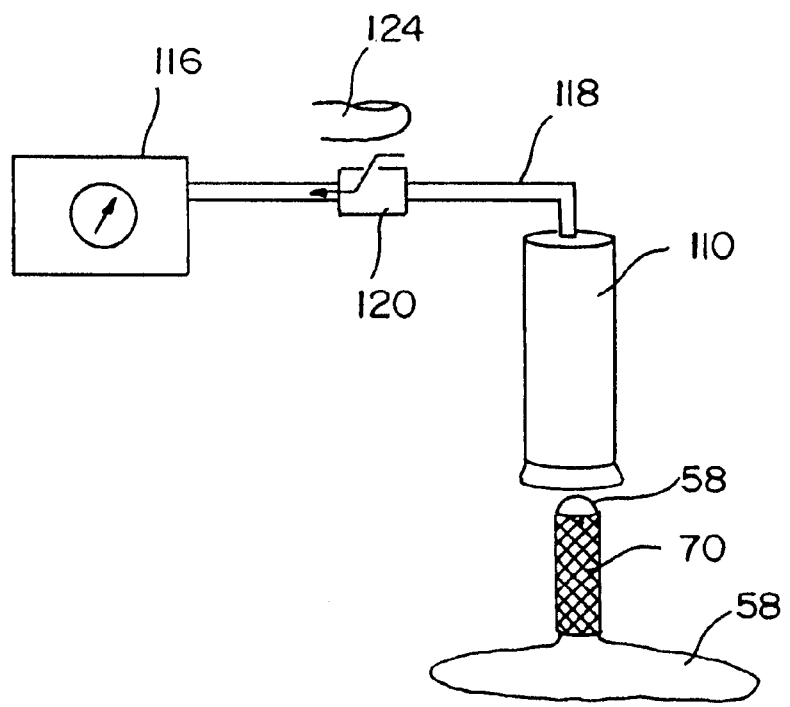
FIG. 14 illustrates a final step in the further method embodiment of deploying the lung constriction device.

FIGS. 12–14 illustrate another embodiment of deploying the lung constriction device 70 in accordance with further aspects of the present invention. Here, rather than using mechanical pulling of the lung tissue into the device 70, vacuum pressure is utilized instead for pulling the lung tissue into the device 70. This permits the procedure to be more automated and potentially less traumatic to the lung tissue being constricted.

As will be noted in FIG. 12, the mandrel or form 110 takes the form of a cylinder having an opened end 112 and a closed end 114. The closed end 114 is coupled to a vacuum source 116 through a conduit 118 and a valve 120. The valve 120 has an aperture 122 which, when closed by, for example, a finger 124, causes the vacuum to be pulled through the conduit 118 and form 110. As illustrated in FIG. 12, the valve is in an opened condition.

The form 110 has a diameter dimension 126 which is substantially greater than the diameter dimension of the device 70 when the device is expandable and in a nonexpanded condition. As seen in FIG. 12, the device 70 has been applied over the form 110 so that the form imparts an expansion force to the device 70. The opened end 112 of the form 110 is in contact with the lung tissue 58 to be constricted.

Referring now to FIG. 13, the finger 124 has now closed the valve 120. The vacuum is now being pulled through the conduit 118 and form 110. This causes the lung tissue 58 to be pulled into the form 110 and the device 70 while the device 70 is in an expanded condition.

After the lung tissue 58 has been pulled into the form 110 and the device 70, the device may be held in position and the form 110 withdrawn from the device 70 and the lung tissue 58. When this is completed, as best seen in FIG. 14, the vacuum suction may be released by opening the valve 120. More importantly, the expansion force of the form 110 on the device 70 is released to permit the device 70 to collapse or contract about the lung tissue 58. The device 70 is now deployed for constricting the lung tissue and providing leak suppression or lung volume reduction, for example.

Again, the device 70 need not be expandable. To that end, the form 110 may have the same or approximately the same dimensions as the device 70. When the vacuum suction pulls the lung tissue 58 into the mandrel or form 110, it will collapse.

After the vacuum suction is terminated and the mandrel 110 removed, the lung tissue 58 will remain in the device 70 in a collapsed condition to be constricted by the device 70.

Figure 15:
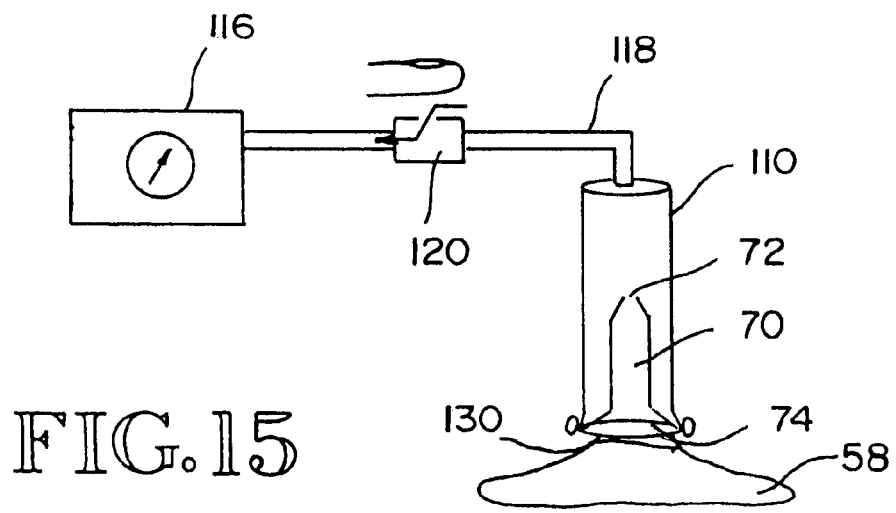
FIG. 15 illustrates an initial step of a still further method of deploying the lung constriction device in accordance with further aspects of the present invention.

FIGS. 15–17 illustrate a further embodiment of deploying the lung constriction device 70. Here again, a vacuum suction is utilized for pulling the lung tissue into the device 70.

As illustrated in FIG. 15, the vacuum source 116, the conduit 118, and the valve 120 are again used to establish the vacuum suction in the form 110. Here, however, the device 70 is positioned inside of the form 110 with the end 74 of the device 70 being stretched and held by the lip 130 of the form 110. As a result, when the valve 120 is closed, the vacuum is pulled through the mandrel 110 and the device 70 due to the opened end 72 of the device 70.

Now, when the lung tissue 58 is brought into engagement with the end 74 of the device 70 and the vacuum is pulled with the closure of valve 120, the lung tissue is pulled directly into the device 70 as illustrated in FIG. 16. The vacuum is pulled until the lung tissue 58 to be constricted preferably extends entirely through the device 70 past the end 72. As will be further noted, the lung tissue itself exerts an expansion force on the device 70 as the lung tissue is pulled into the device 70.

After the lung tissue 58 has been pulled into the device 70, the end 74 of the device 70 may be released from the lip 130 of the form 110 to permit the form 110 to be withdrawn from the device 70. When this is completed, as best seen in FIG. 17, the vacuum suction may be released by opening the valve 120. The release of the vacuum also releases the expansion force on the device 70. With the expansion force released, the device is permitted to collapse or contract about the lung tissue 58. The device 70 is now deployed for constricting the lung tissue and providing leak suppression or lung volume reduction, for example.

Once again, the device 70 need not be expandable. To that end, the form or mandrel 110 may be of the same dimension or slightly larger dimension than the device 70 to permit an effective seal between the lip 130 of mandrel or form 110 and the end 74 of the device 70. The vacuum suction will still be pulled through the form 110 and the device 70. As the vacuum suction pulls the lung tissue into the device 70, the lung tissue collapses. When the vacuum is released and the form 110 is removed, the collapsed lung tissue will remain constricted in the device 70 to provide, for example, lung leakage suppression or lung volume reduction.

Figure 18:
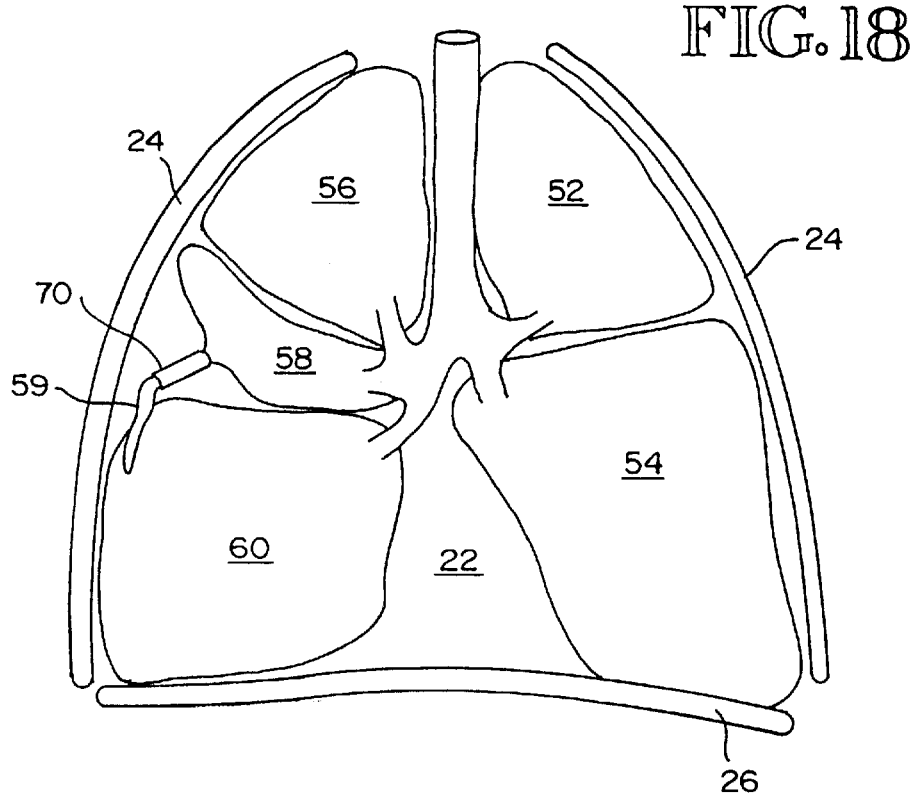
FIG. 18 is a sectional view illustrating the lung constricting apparatus constricting a lung portion to be sectioned for lung volume reduction.

Referring now to FIG. 18, it illustrates a manner in which the lung constriction apparatus 70 may be employed for effecting lung volume reduction to a greater extent. In accordance with this embodiment, the lung portion 59 of lobe 58 has been pulled through the device 70 and is being constricted by the device 70. The device 70 and the manner of pulling the lung portion 59 therethrough may conform to any of the embodiments previously described herein.

Figure 19:
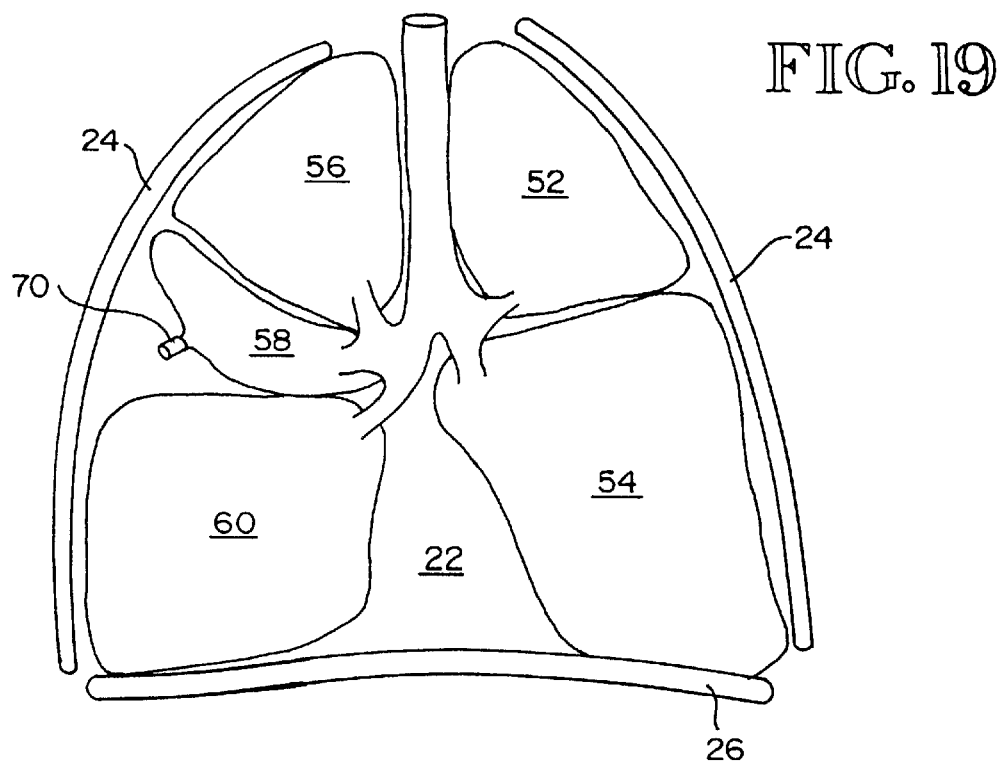
FIG. 19 illustrates the lung portion after being sectioned in accordance with a further embodiment of the present invention.

In accordance with this embodiment, the device 70 is formed of severable material, such as, any of the materials previously described. This enables the device or jacket 70 to be severed or cut intermediate its ends as illustrated in FIG. 19 to section the lung portion 59. The portion of the device 70 remaining on the lobe 58 continues to constrict the lung tissue therein to form an effective seal from leakage. Hence, in accordance with this embodiment of the present invention, lung volume reduction is rendered an available treatment while negating the need of conventional lung sectioning and suturing thus avoiding the potentially severe complications which accompany those procedures.

While particular embodiments of the present invention have been shown and described, modifications may be made, and it is therefore intended in the appended claims to cover all such changes and modifications which may fall within the true spirit and scope of the invention.

What is claimed is:

1. A lung constriction device comprising a jacket of flexible material configured to cover only a portion of a lung, the jacket having a pair of opened ends to permit the lung portion to be drawn into the jacket and the jacket being dimensioned to constrict and collapse the lung portion.

2. The device of claim 1 wherein the jacket is formed of elastic material.

3. The device of claim 1 wherein the jacket is formed of a mesh material.

4. The device of claim 1 wherein the jacket is formed of one of silicone rubber, polyester, polyurethane, nylon, polytetraflouroethylene, expanded polytetraflouroethylene, polyester and polyurethane, and nylon and polyurethane.

5. The device of claim 1 wherein the jacket is formed of an expandable mesh material.

6. The device of claim 1 wherein the jacket is formed of a severable material to permit the device to be severed intermediate its ends.

7. A lung constriction device comprising a member formed of expandable material, the member being configured for receiving only a portion of a lung when forced into an expanded enlarged condition by an expansion force, and contractible about the lung portion upon release of the expansion force for constricting and collapsing the lung portion.

8. The device of claim 7 wherein the member has a hollow, substantially cylindrical configuration when in a nonexpanded condition.

9. The device of claim 7 wherein the member includes a first opened end for receiving the lung portion.

10. The device of claim 9 wherein the member includes a second opened end for permitting the lung portion to extend through the member.

11. The device of claim 7 wherein the member is formed of one of silicone rubber, polyurethane, expanded polytetraflouroethylene, nylon and polyurethane, and polyester and polyurethane.

12. The device of claim 7 wherein the member is formed of an expandable mesh material.

13. The device of claim 7 wherein the member is formed of a severable material.

14. A method of constricting and collapsing only a portion of a lung, the method including the steps of:

providing a jacket formed of flexible material and configured to cover only a portion of the lung; and drawing the lung portion into the jacket to constrict and collapse the lung portion.

15. The method of claim 14 wherein the jacket is dimensioned to constrict the lung portion and wherein the drawing step includes collapsing the lung portion while drawing the lung portion into the jacket.

16. The method of claim 15 wherein the drawing step includes physically pulling the lung portion into the jacket.

17. The method of claim 14 wherein the jacket is formed of expandable material and wherein the method includes the further steps of applying an expansion force to the jacket to enlarge the jacket dimensions and releasing the expansion force on the jacket after the drawing step to permit the jacket to collapse about the lung portion for constricting the lung portion.

18. The method of claim 17 wherein the drawing step includes physically pulling the lung portion.

19. The method of claim 14 including the further step of severing the jacket after drawing the lung portion into the jacket to section the lung portion.

20. A method of constricting at least a portion of a lung, the method including the steps of:

providing a jacket formed of flexible material and configured to cover the lung portion;

drawing the lung portion into the jacket; and positioning the jacket on a mandrel, wherein the lung portion is physically pulled into the mandrel, and the method further including the step of removing the mandrel from the jacket and the lung portion to leave the lung portion constricted in the jacket.

21. A method of constricting at least a portion of a lung, the method including the steps of:
  providing a jacket formed of flexible material and configured to cover the lung portion; and
  drawing the lung portion into the jacket, wherein the jacket is dimensioned to constrict the lung portion, wherein the drawing step includes collapsing the lung portion while drawing the lung portion into the jacket, and wherein the drawing step includes applying a vacuum suction to the lung portion.

22. The method of claim 21 further including the step of positioning the jacket on a mandrel, wherein the vacuum suction is applied to the lung portion through the mandrel, and the method further including the step of removing the mandrel from the jacket and the lung portion to leave the lung portion constricted in the jacket.

23. The method of claim 21 further including the step of positioning the jacket within a mandrel, wherein the vacuum suction is applied to the lung portion through the mandrel and the jacket to pull the lung portion directly into the jacket, and the method further including the step of removing the mandrel from the jacket.

24. A method of constricting at least a portion of a lung, the method including the steps of:
  providing a jacket formed of flexible material and configured to cover the lung portion; and
  drawing the lung portion into the jacket, wherein the jacket is formed of expandable material, wherein the method includes the further steps of applying an expansion force to the jacket to enlarge the jacket dimensions and releasing the expansion force on the jacket after the drawing step to permit the jacket to collapse about the lung portion for constricting the lung portion, and wherein the applying step includes positioning the jacket on a mandrel.

25. The method of claim 24 wherein the applying step further includes expanding the mandrel after positioning the jacket on the mandrel.

26. The method of claim 24 wherein the drawing step includes applying a vacuum suction to the lung portion through the mandrel to draw the lung portion into the mandrel and wherein the releasing step includes removing the jacket from the mandrel.

27. The method of claim 26 wherein the releasing step further includes terminating the vacuum suction prior to removing the jacket from the mandrel.

28. A method of constricting at least a portion of a lung, the method including the steps of:
  providing a jacket formed of flexible material and configured to cover the lung portion; and
  drawing the lung portion into the jacket, wherein the jacket is formed of expandable material, wherein the method includes the further steps of applying an expansion force to the jacket to enlarge the jacket dimensions and releasing the expansion force on the jacket after the drawing step to permit the jacket to collapse about the lung portion for constricting the lung portion, and wherein the drawing step includes applying a vacuum suction to the lung portion.

29. A method of constricting at least a portion of a lung, the method including the steps of:
  providing a jacket formed of flexible material and configured to cover the lung portion; and
  drawing the lung portion into the jacket, wherein the jacket is formed of expandable material, wherein the method includes the further steps of applying an expansion force to the jacket to enlarge the jacket dimensions and releasing the expansion force on the jacket after the drawing step to permit the jacket to collapse about the lung portion for constricting the lung portion, and wherein the method further includes the steps of positioning the jacket within a mandrel, and applying a vacuum suction to the lung portion through the mandrel and the jacket to cause the lung portion to be drawn into the jacket and the jacket to be expanded by the lung portion drawn by the vacuum suction.

30. The method of claim 29 wherein the releasing step includes terminating the vacuum suction.

31. A method of reducing the size of a lung, the method including the steps of:
  providing a jacket of severable material configured and dimensioned to constrict and seal lung tissue;
  drawing a portion of the lung into the jacket to constrict and seal lung tissue of the lung portion; and
  severing the jacket to section the lung.

32. The method of claim 31 wherein the jacket includes a pair of opened ends and wherein the drawing step includes drawing the lung portion through the jacket.

33. A method of sectioning body tissue, the method including the steps of:
  providing a jacket of severable material configured and dimensioned to constrict and seal the body tissue;
  drawing the body tissue into the jacket to constrict and seal the body tissue; and
  severing the jacket to section the body tissue.

34. The method of claim 33 wherein the jacket includes a pair of opened ends and wherein the drawing step includes drawing the body tissue through the jacket.

35. A system for sectioning body tissue, the system comprising:
  a jacket of severable material configured and dimensioned to constrict and seal the body tissue;
  means for drawing the body tissue into the jacket to constrict and seal the body tissue; and
  means for severing the jacket to section the body tissue.

36. The system of claim 35 wherein the jacket is formed of an elastic material.

37. A device for use in sectioning body tissue comprising a jacket of severable material configured to cover the body tissue, the jacket having a pair of opened ends to permit the body tissue to be drawn into the jacket and the jacket being dimensioned to constrict and seal the body tissue.

38. The device of claim 37 wherein the jacket is formed of elastic material for collapsing about the body tissue.

39. A lung constriction device comprising a jacket of flexible material configured to cover only a portion of a lung, the jacket having a pair of opened ends to permit the lung portion to be drawn into the jacket and the jacket being dimensioned to constrict, collapse, and disable the lung portion.

40. A lung constriction device comprising a member formed of expandable material, the member being configured for receiving only a portion of a lung when forced into an expanded enlarged condition by an expansion force, and contractible about the lung portion upon release of the expansion force for constricting, collapsing, and disabling the lung portion.

41. A method of constricting, collapsing, and disabling a portion of a lung, the method including the steps of:
  providing a jacket formed of flexible material and configured to cover the lung portion; and
  drawing the lung portion into the jacket to constrict, collapse, and disable the lung portion.

* * * * *